United States Patent
Golini

(10) Patent No.: US 6,399,661 B1
(45) Date of Patent: Jun. 4, 2002

(54) ORAL CREATINE SUPPLEMENT AND METHOD FOR MAKING SAME

(76) Inventor: Jeffrey M. Golini, 1831 Main St., Billings, MT (US) 59105

( * ) Notice: Subject to any disclaimer, the term of this patent is extended or adjusted under 35 U.S.C. 154(b) by 0 days.

(21) Appl. No.: 09/892,890

(22) Filed: Jun. 26, 2001

Related U.S. Application Data

(60) Provisional application No. 60/214,182, filed on Jun. 26, 2000.

(51) Int. Cl.⁷ .............................................. A61K 31/195
(52) U.S. Cl. ...................................... 514/565
(58) Field of Search ........................................ 514/505

(56) References Cited

U.S. PATENT DOCUMENTS

| | | |
|---|---|---|
| 3,907,644 A | 9/1975 | Mollering et al. |
| 3,912,588 A | 10/1975 | Mollering et al. |
| 5,612,375 A | 3/1997 | Sueoka |
| 5,773,473 A | 6/1998 | Green et al. |
| 5,886,040 A | 3/1999 | Fang |
| 5,908,864 A | 6/1999 | Casey |
| 5,925,378 A | 7/1999 | Carnazzo |
| 5,968,544 A | 10/1999 | Howard et al. |
| 5,968,900 A | 10/1999 | Greenhaff et al. |
| 5,973,005 A * | 10/1999 | D'Amelio et al. .......... 514/565 |
| 5,973,199 A * | 10/1999 | Negrisoli et al. .......... 562/560 |
| 6,013,290 A | 1/2000 | Weinstein et al. |
| 6,080,553 A | 6/2000 | Sogabe et al. |
| 6,114,379 A | 9/2000 | Wheelwright et al. |
| 6,136,339 A | 10/2000 | Gardiner |
| 6,168,802 B1 | 1/2001 | Howard et al. |
| 6,172,114 B1 | 1/2001 | McCabe |

* cited by examiner

*Primary Examiner*—James H. Reamer
(74) *Attorney, Agent, or Firm*—Richard C. Conover

(57) ABSTRACT

The present invention relates to an oral creatine supplement and the method of making this supplement which includes mixing an alkaline powder with a powdered creatine until the pH of the mixture is in the range between 7–14. A powdered additive is added to the mixture for improving sweetness and taste. Finally, a further alkaline powder is added to the mixture to adjust the pH of the mixture to a range between 7–14. This mixture is then mixed with water prior to ingestion.

21 Claims, 3 Drawing Sheets

| PH | Time for conversion of 1g creatine to creatinine in 1 liter at given ph (min) |
|---|---|
| 2 | 0.4274 |
| 4 | 2.8081 |
| 6 | 8.4465 |
| 8 | 18.4507 |
| 10 | 33.8236 |
| 12 | 55.4979 |
| 14 | Never |

FIG. 3

ORAL CREATINE SUPPLEMENT AND METHOD FOR MAKING SAME

This application claims the benefit of provisional application 60/214,182 filed Jun. 26, 2000.

BACKGROUND OF INVENTION

The present invention relates to an oral creatine supplement, and the method for making this supplement.

Taking creatine orally has been used to increase creatine and creatine phosphate stores in the human body. This is important for athletes because creatine aids in the process of creating energy usable by muscles of the athlete.

When an athlete exercises or tenses a muscle, energy is required for the muscle to function properly. The energy it uses comes from several different sources, but primarily from nutrients obtained from food. These nutrients are broken down by natural processes occurring within the human body, and new compounds formed which are used to develop energy used by muscles. One of these compounds is adenosine triphosphate (ATP). When muscle energy is needed this ATP is broken down one step further into a chemical called adenosine diphosphate (ADP). This process releases energy which is then used by the contracting muscles. Without sufficient ATP, muscles do not perform properly.

Known energy increasers and stimulants have only superficially energized the body, and do not increase the body's ability to produce it's own ATP stores.

Muscle can store only limited amounts of ATP. As a result, it has been found that with about 5–10 seconds of muscle exertion, the amount of stored ATP is depleted. This results in muscle failure and fatigue. When this happens, the body tries to restore its immediate source of ATP by borrowing a high energy phosphate from a chemical called creatine phosphate (CP). Muscle cells store the chemical, CP, in the same way it stores ATP. If high intensity exercise goes beyond 10 seconds, the body will continue to try and restore its ATP levels by a process called glycolysis. This process is complicated and is a slow method of restoring ATP levels. This is a special problem for anaerobic athletes who require instant energy to maintain and sustain high powered muscle contractions.

By orally supplementing with creatine, an athlete can enhance his body's storage levels of CP. As the muscle runs out of ATP, it can recharge itself by borrowing this CP molecule. Research has shown that by supplementing with 5 grams of creatine, 4–6 times a day, for two or more days, the human body showed a significant increase in total creatine concentration.

ATP or CP cannot be ingested directly by athletes because these chemicals are destroyed by the digestive system of the athlete. However, it has been found that creatine can be ingested and converted by the body to CP. The resulting cellular concentrations of creatine after administration, is stable and is not prone to dissipation.

The most commonly used oral creatine supplement is creatine monohydrate. The most commonly used amounts have varied from 20 to 30 grams daily. It has been taken in powder, capsule, tablet hand liquid form. The creatine is mixed with or taken with water, fruit juice, acidic effervescent drink or acidic fruit flavored drinks.

Other that creatine monohydrate, other forms of creatine have also been used, such as creatine citrate and also creatine pyruvate. These other forms of creatine are administered similar to the method of administrating creatine monohydrate.

The main problem with all existing creatine supplementation is the ability to deliver creatine in a usable form by the human body. Research has shown that known creatine delivery systems actually have the human body ingesting creatinine, a poison and toxic byproduct. It is believed that the main reason for complaints resulting from creatine consumption, namely, stomach cramps, edema, bloodedness and dehydration, is caused by the body's defense to this toxic compound.

The known oral creatine supplements are dissolved in acidic solutions having a pH range of from 3–6. Research has shown that at these pH levels, the rate of conversion of creatine to creatinine is almost instantaneous.

From the above, it may be ascertained that a need exists for a method of enhancing the delivery of usable creatine to humans without substantial creatinine being formed. Further, a need exists for an oral creatine supplement that is in the form of a powder, capsule, tablet or liquid that is stable when mixed with water or taken premixed or in pill form.

SUMMARY OF INVENTION

The present invention relates to an oral creatine supplement and the method of making this supplement which includes mixing an alkaline powder with a powdered creatine until the pH of the mixture is in the range between 7–14. A powdered additive is added to the mixture for improving sweetness and taste. Finally, a further alkaline powder is added to the mixture to adjust the pH of the mixture to a range between 7–14. This mixture is then mixed with water prior to ingestion.

DESCRIPTION OF THE DRAWINGS

In order that the invention may be clearly understood and readily carried into effect, a preferred embodiment of the invention will now be described, by way of example only, with reference to the accompanying drawings wherein:

FIG. 3 is a chart showing time in minutes for conversion of 1 g creatine to creatinine in 2 liter at given pH.

DESCRIPTION OF A PREFERRED EMBODIMENT

Figure 1:
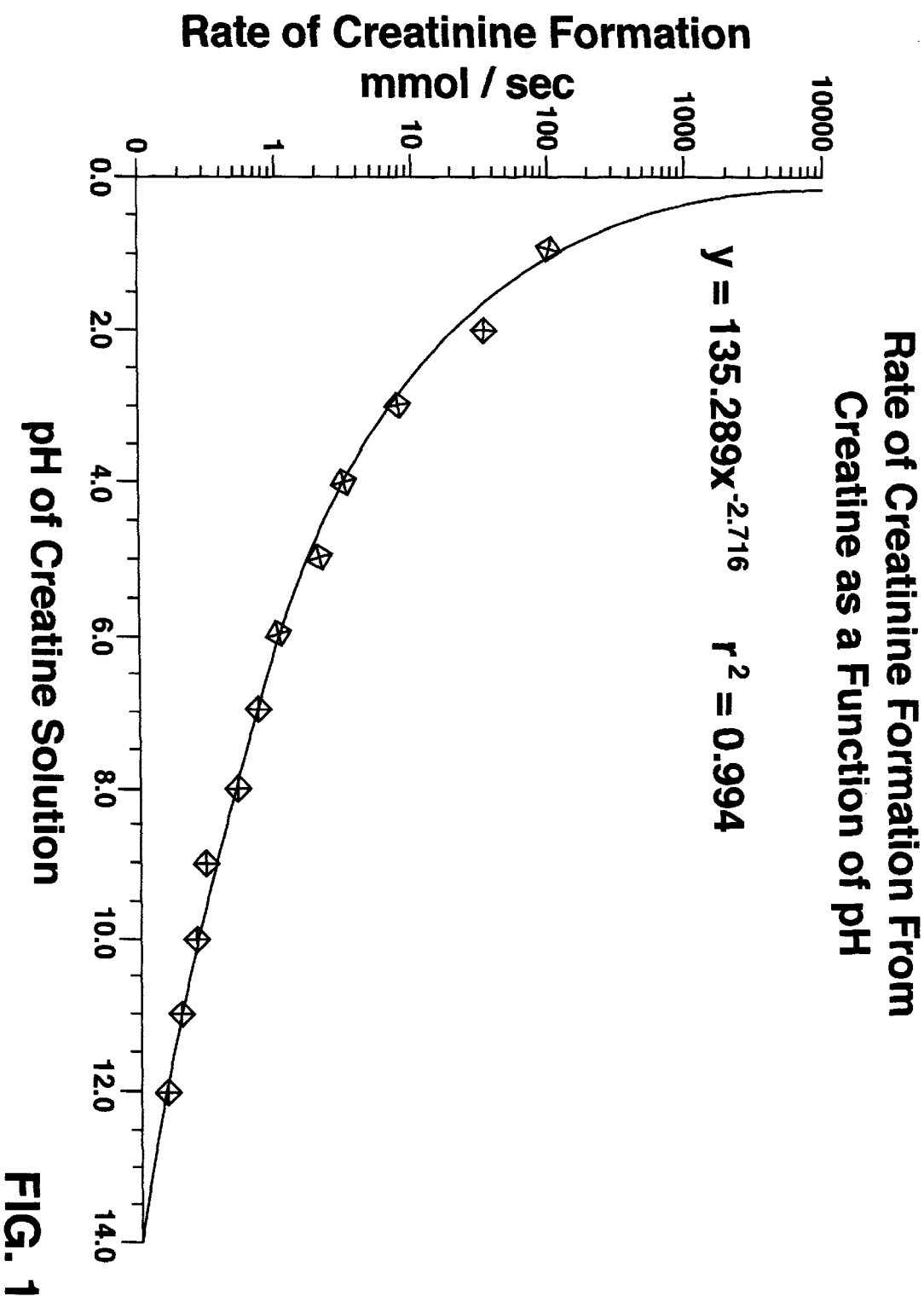
FIG. 1 is a graph showing rate of creatinine formation from creatine as a function of pH.
Figure 2:
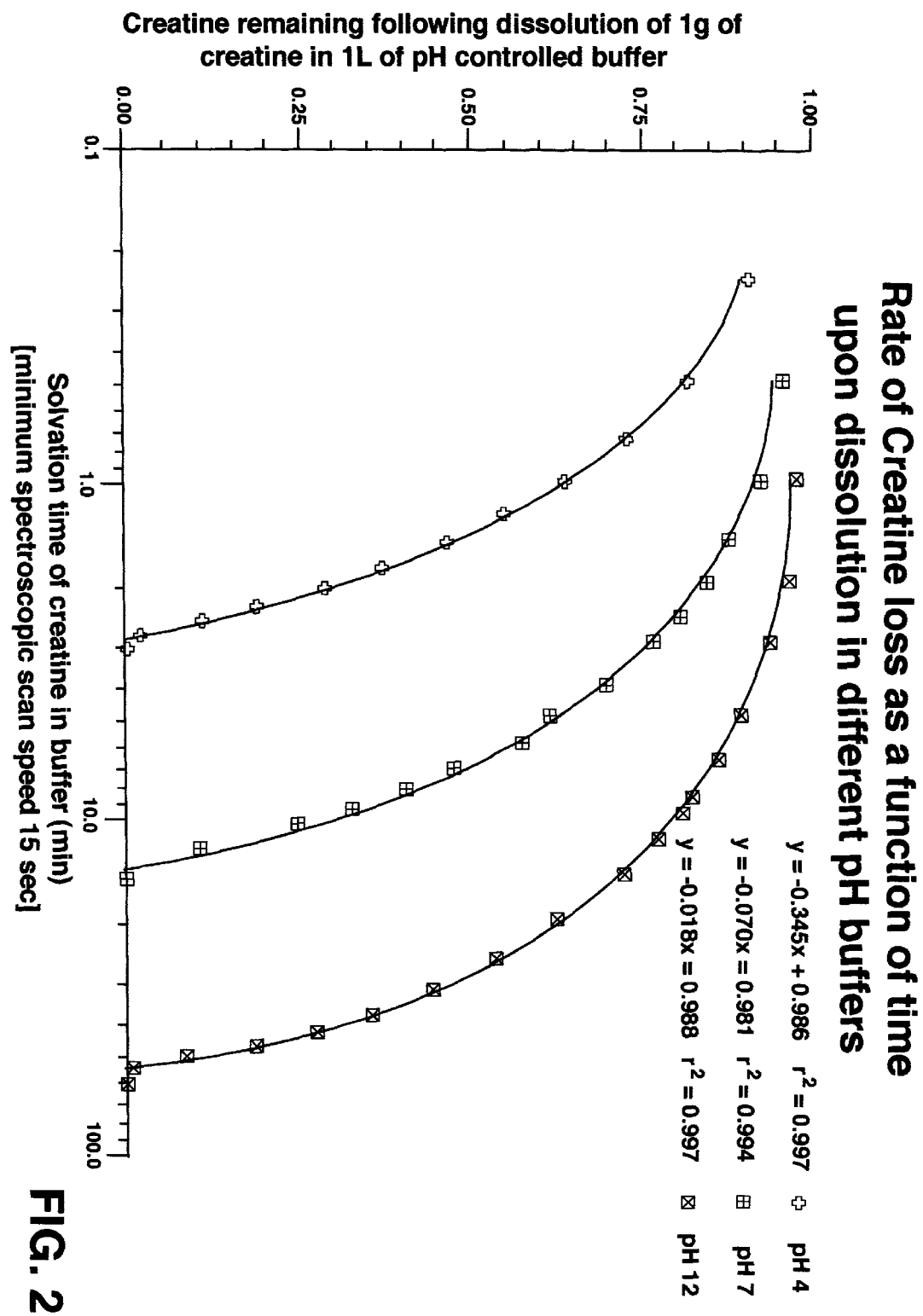
FIG. 2 is a graph showing rate of creatine loss as a function of time upon dissolution in different pH buffers.

The rate of creatinine formation from creatine as a function of pH is shown in FIG. 1 in accordance with research conducted by the inventor. In FIG. 2, the rate of creatine loss as a function of time upon dissolution in different pH buffers is shown. Clearly the higher the pH, the higher the creatine remaining following dissolution in a pH buffer. FIG. 3 shows a summary of experiments showing the rate of conversion of one gram of creatine to creatinine in various pH solutions. This chart shows that the rate of conversion is substantially slowed by increasing the pH of the solution.

In accordance with the present invention, the inventor has created a buffered delivery system wherein creatine monohydrate is dissolved in a solution having a pH greater than 7. The inventor has developed five separate systems for delivery of creatine in an oral supplement.

The first is a powder mix having the following formulation:

| | |
|---|---|
| Creatine Monohydrate | 5000 mg |
| Sugar (from dextrose, fructose, sucrose, or a type of sugar) | 10–15 g |
| Maltodextrin (from corn and/or rice) | 5–10 g |
| Soda Ash | 50 mg–1.5 g |
| Natural and/or Artificial Flavors | 2 g |
| Magnesium Glycerol Phosphate | 500 mg |
| Aspartame, Acesulfame K, Sucralose and/or Stevia Extract (Powder mix can be with/without flavors, sugars or sweeteners) | 200 mg |

The method for preparing the powder mix includes placing the 5000 mg of creatine monohydrate in a mixing vessel. The soda ash is then added to adjust the pH of the mixture from 7–14. After the pH has been adjusted, the sugar, natural and/or artificial flavors, and the aspartame, acesulfame K, sucralose and/or stevia extract are added to adjust the mixture for desired taste and desired sweetness. The pH of the mixture is again checked and magnesium glycerol phosphate is added to adjust the pH to be between 7 and 14. The powder is then bottled for distribution.

In capsule form, the capsule includes the following formulation:

| | |
|---|---|
| Creatine Monohydrate | 1000 mg |
| Maltodextrin | 200 mg |
| Magnesium Stearate | 5 mg |
| Magnesium Glycerol Phosphate | 25 mg |
| Soda Ash | 5–1000 mg |
| Natural and/or Artificial Flavors | 20 mg |

The method for making capsules is to place 1000 mg of creatine monohydrate in a mixing vessel. The pH is adjusted to be between 7 and 14 by adding soda ash. The maltodextrin, magnesium stearate (a flow agent) and natural and/or artificial flavors are added to desired taste and sweetness. The pH is again checked, and magnesium glycerol phosphate is added to adjust the pH to be between 7 and 14. The mixed powder is then processed by a conventional encapsulation machine which prepares capsules of the powder.

A capsule with this formulation is swallowed by a user and dissolves in the solution present in the stomach.

In tablet form, the formulation is as follows:

| | |
|---|---|
| Creatine Monohydrate | 250 mg |
| Sorbitol | 400 mg |
| Microcrystalline Cellulose | 50 mg |
| Magnesium Stearate | 5 mg |
| Magnesium Glycerol Phosphate | 25 mg |
| Soda Ash | 5–500 mg |

In preparing the tablets, creatine monohydrate is placed in a mixing vessel and soda ash is added to adjust the pH from between 7 and 14. Sorbitol, which is a hardener, and microcrystalline cellulose, which is a binder, is added to the mixture, as well as magnesium stearate, which is a stabilizer, in preparation for forming tablets. The pH of the mixture is then checked and magnesium glycerol phosphate is then added to adjust the pH to be between 7 and 14. The powder is then processed by a conventional machine which compresses the powder into tablets.

A tablet with this formulation is swallowed by a user and dissolves in the solution present in the stomach.

In liquid form, the formulation is as follows:

| | |
|---|---|
| Creatine Monohydrate | 3 grams |
| Water | 1–30 ml |
| Glycerine | 1–30 ml |
| Magnesium Glycerol Phosphate | 25 mg |
| Natural and/or Artificial Flavors | 5 ml |
| Soda Ash | 50–1000 mg |
| Potassium Sorbate | 200 mcg |

In preparing the liquid form, water and creatine monohydrate are mixed together in a mixing vessel. Soda ash is added to adjust the pH to be between 7 and 14. The glycerine, which acts as a base and preservative, together with potassium sorbate, which acts as a stabilizer and preservative, are added to the admixture. Further, natural and/or artificial flavors are added to adjust the mixture for desired taste and sweetness. The pH is again checked, and magnesium glycerol phosphate is then added to adjust the pH to be between 7 and 14. The resulting liquid is then bottled for distribution.

With this liquid form, the product is ingested directly.

In a softgel form, the formulation is as follows:

| | |
|---|---|
| Creatine Monohydrate | 100 mg |
| Sugar | 300 mg |
| Chocolate | 50 mg |
| Soy Bean Oil | 500 mg |
| Magnesium Glycerol Phosphate | 25 mg |
| Soda Ash | 5–1000 mg |

The method for making the softgel includes placing the creatine monohydrate in a mixing vessel. Soda ash is then added to adjust the pH to be between 7 and 14. Next, the sugar, chocolate and soy bean oil, which acts as a base for the gel, is added to the mixture. Again, the pH is checked, and magnesium glycerol phosphate is added to adjust the pH to be between 7 and 14. The resulting gel is then placed in bottles for distribution.

With these formulations, the pH of the solution is above 7, and the beneficial results shown in FIGS. 1–3 are thereby obtained.

It should be understood that organic or inorganic substances could be used with equally beneficial results to raise the pH of the solution. For example, hydroxides, carbonates, bicarbonates, chlorides, tree latex or phosphates could be used.

Further, the creatine used could be creatine monohydrate as described in the above formulations, or could be creatine phosphate, creatine pyruvate or creatine citrate.

The types, combination and amounts of buffers can vary with various delivery forms, flavors, and combination type products.

The method for enhancing a stable concentration of creatine in a human includes dissolving the creatine powder into water or any other type of fluid. Once the mixture has been mixed, the solution is ingested immediately and an effective amount of creatine is absorbed. The capsule, tablet and liquid form can be ingested as is.

This buffered delivery system enhances the delivery of usable creatine to the person taking the supplement, and overcomes the problems caused when creatine is converted to creatinine. The higher the pH, the more creatine a human will ingest.

While the fundamental novel features of the invention have been shown and described, it should be understood that various substitutions, modifications and variations may be made by those skilled in the art without departing from the spirit or scope of the invention. Accordingly, all such modifications or variations are included in the scope of the invention as defined by the following claims:

I claim:

1. A process for producing a creatine mixture for ingestion comprising the steps of:

mixing an alkaline powder with a powdered creatine to adjust the pH of the mixture to a range between 7–14;

adding a powdered additive to the mixture for improving sweetness and taste; and adding a further alkaline powder to the mixture to adjust the pH of the mixture to a range between 7–14.

2. The method according to claim 1 wherein the alkaline powder is comprised of soda ash.

3. The method according to claim 1 wherein the alkaline powder is comprised of magnesium glycerol phosphate.

4. The method according to claim 1 wherein the alkaline powder is selected from a hydroxide, carbonate, bicarbonate, chloride, tree latex or a phosphate.

5. The method according to claim 1 wherein the creatine powder is comprised of creatine monohydrate.

6. The method according to claim 1 wherein the creatine powder is comprised of creatine phosphate.

7. The method according to claim 1 wherein the creatine powder is comprised of creatine pyruvate.

8. The method according to claim 1 wherein the creatine powder is comprised of creatine citrate.

9. The method according to claim 1 further including the step of mixing the mixed creatine powder with water prior to ingestion.

10. The method of claim 1 further including the steps of adding a flow agent and the step of encapsulating the mixture in a capsule.

11. The method according to claim 10 wherein the flow agent is comprised of magnesium stearate.

12. The method according to claim 1 further including the steps of adding a hardener material, a binder material, and a flow agent, and the further step of compressing the mixture into tablets.

13. The method according to claim 12 wherein the hardener material is comprised of sorbitol.

14. The method according to claim 12 wherein the binder material is comprised of microcrystalline cellulose.

15. The method according to claim 12 wherein the flow agent is comprised of magnesium stearate.

16. The method according to claim 1 further including the step of adding water to the mixture together with a base material and a stabilizer material for forming a creatine solution.

17. The method according to claim 16 wherein the base material is comprised of glycerine.

18. The method according to claim 16 wherein the stabilizer material is comprised of potassium sorbate.

19. The method according to claim 1 further including the step of adding a gel base material to the mixture for forming a soft gel.

20. The method according to claim 1 wherein the gel base material is comprised of soy bean oil.

21. A creatine mixture for ingestion which is produced by a process comprising the steps of:

mixing an alkaline powder with a powdered creatine to adjust the pH of the mixture to a range between 7–14;

adding a powdered additive to the mixture for improving sweetness and taste; and adding a further alkaline powder to the mixture to adjust the pH of the mixture to a range between 7–14.

* * * * *